United States Patent
Bicz

[19]

[11] Patent Number: 6,164,135

[45] Date of Patent: Dec. 26, 2000

[54] METHOD AND DEVICE FOR THE STRUCTURE ANALYSIS AND/OR FOR DETECTING THE POSITION OF LAYERED OBJECTS

[75] Inventor: Wieslaw Bicz, Wroclaw, Poland

[73] Assignee: Sonident Anstalt, Vaduz, Liechtenstein

[21] Appl. No.: 09/029,955

[22] PCT Filed: Sep. 6, 1996

[86] PCT No.: PCT/EP96/03916

§ 371 Date: Jun. 5, 1998

§ 102(e) Date: Jun. 5, 1998

[87] PCT Pub. No.: WO97/08990

PCT Pub. Date: Mar. 13, 1997

[30] Foreign Application Priority Data

Sep. 7, 1995 [DE] Germany ............................ 195 33 007

[51] Int. Cl.[7] ............................ H01L 41/08; G08C 21/00
[52] U.S. Cl. .................... 73/602; 178/18.04; 310/313 R; 310/313 D; 345/173; 345/177
[58] Field of Search ............................ 73/597, 598, 599, 73/600, 602, 627, 628, 629, 645, 646; 178/18.01, 18.03, 18.04, 19.01, 19.02; 310/313 R, 313 B, 313 D; 367/907; 345/173, 177, 176

[56] References Cited

U.S. PATENT DOCUMENTS

| | | | |
|---|---|---|---|
| 5,334,805 | 8/1994 | Knowles et al. | 178/18 |
| 5,573,077 | 11/1996 | Knowles | 178/19 |
| 5,886,452 | 3/1999 | Toda | 310/313 R |

FOREIGN PATENT DOCUMENTS

| | | | |
|---|---|---|---|
| 2195289 | 8/1990 | Japan | 178/18 |

*Primary Examiner*—Hezron Williams
*Assistant Examiner*—Rose M. Miller
*Attorney, Agent, or Firm*—Herbert Dubno

[57] ABSTRACT

A method and an apparatus for analyzing a structure, for example, a fingerprint or a hand print, in which the finger or hand is placed upon a plate which forms an ultrasonic wave waveguide and ultrasonic radiation, launched into the waveguide parallel to the surface against which the object is placed. The reflected and backscattered waves are analyzed utilizing horizontally polarized ultrasonic shear waves propagated in the body from at least one transducer at a side of the body. The pickup transducer can also be provided on the side of the body.

12 Claims, 3 Drawing Sheets

METHOD AND DEVICE FOR THE STRUCTURE ANALYSIS AND/OR FOR DETECTING THE POSITION OF LAYERED OBJECTS

CROSS REFERENCE TO RELATED APPLICATION

This application is a national stage of PCT/EP96/03916 filed Sep. 6, 1996 and based upon German application 195 33 007.2 of Sep. 7, 1995, and 196 36 124.9 of Sep. 6, 1996 under the International Convention.

FIELD OF THE INVENTION

The invention relates to an apparatus for structural analysis and/or position detection of stratified objects by means of ultrasonic waves, with one or more ultrasonic generators and ultrasonic receivers, as well as a support surface for the object.

BACKGROUND OF THE INVENTION

Devices analyzing the structure of stratified objects by means of ultrasound are already known, such as for instance from the EP 0 262 186. The known devices are based on the principle of reflection tomography. This principle applied to fingerprints according to the mentioned European Patent was presented at the Conference of Acoustical Imaging in Florence in 1995 and published in the respective Proceedings under the title "Ultrasonic setup for fingerprint pattern detection and evaluation". In the known references, the object placed on a support plate is subjected to ultrasound waves coming from a generator arranged oppositely thereto in a liquid filled housing. Either several generators and several receivers are arranged on the housing wall opposite to the support surface, or the generator and also the receiver are movable on a carrier along a trajectory. In this way the finger tip or any other object on any point of the support plate can be detected. The waves reflected and back-scattered by the object are received by a receiver which transmits the information about the intensity and/or the phase of backscattering and reflection to a computer for analysis and recording, optionally via an amplifier, a timing device, possibly also a detector.

The ultrasonic waves to which the finger or other objects are exposed are bulk waves originating from the generator/generators in the same manner as the backscattered and reflected sound waves, which are in the range of 2 MHz and above.

The production of devices of the known kind has proven to be complicated, particularly because the housing is filled with liquid. This requires the housing to be perfectly sealed off and the arrangement of the transducers in the liquid is also fraught with problems. Furthermore due to the liquid-filled housing and the use of bulk waves, these devices are also relatively large, since a certain size of the object can not be reduced. They also do not allow for a large size of the support plate, which makes impossible the analysis of objects with a large surface, e.g. human hands.

Further devices used purely for position detection have become known. Such a contact sensor is described in the abstract of JP-A-2 195 289. The latter consists of a tube serving as a wave guide, at whose open end an ultrasound transducer serving a sender, or receiver, to which a transmitting and time-measuring circuit, as well as a distance calculator are connected. Depending on the mechanical pressure on the wave guide, the reflection of the ultrasonic wave is determined and therewith the pressure point is calculated. A structural analysis can not be performed with the device of the aforementioned application.

There are also other known device which detect the position of an object, such as the position of a finger on a surface, e.g. a display (see also EP 0 557 446 and 0 523 200). However these devices are not capable of analyzing the structure of the object, e. g. the finger, since they have poor resolution and also because they are not intended for this purpose. Also their modus operandi is different, since these devices use only the attenuation of the ultrasonic waves which are generated by the object, which in principle can not give information about the structure.

OBJECTS OF THE INVENTION

The object of the invention is to provide a method consists in proposing a method and an apparatus for the analysis of surface structures, as well as of the areas close to the surface and/or the position of objects, which permit a more compact wave pattern and make possible a flatter and more compact construction. Structurally the device should require less technical effort for equal analysis results.

SUMMARY OF THE INVENTION

These objects are attained in accordance with the invention, in a method for analyzing surface structures and structures close to the surface of objects and/or for the position detection of object by means of ultrasonic waves, with an ultrasonic wave transmitter and an ultrasonic wave receiver, as well as a plate serving as a support surface for the object. According to the invention the object resting on the plate is exposed to horizontally polarized ultrasonic waves, i.e. so-called shear waves (SH-waves), whereby the waves reflected and/or back-scattered from the object are guided along the solid body and transmitted for analysis to the transducers.

A plate-shaped solid body suited for the guidance of unidimensional or two-dimensional waves is used as support surface, to which laterally arranged ultrasonic wave senders for generating shear waves and receivers for their reception are assigned, whereby the sending and receiving can be carried out by a transducer.

Surprisingly it has been established in tests that also ultrasonic waves guided in this manner can deliver clear and reproducible analyses of the structure and/or the position of the objects. One starts with a plate of any desired dimensions, with laterally arranged senders or senders and receivers. One sender or receiver can thus be arranged underneath the plate. According to the invention the exposure to sonic waves takes place with shear waves (SH-waves)i.e. waves which are horizontally polarized. The plate can consist of glass, metal or crystal with a low degree of absorption. Of course it is also possible to provide transducers on the plate sides, which at the same time are senders and receivers, since also in the case of ultrasonic waves generated and/or received laterally with respect to the support plate, guided along the plate surface, a reproducible and strong reflection and/or scattering takes place at the structure adjoining the plate surface.

At least one surface of the plate forms the boundry which guides the wave two-dimensionally. Thereby it does not matter whether a guided or a normal wave is generated, but the wave reflected and/or backscattered by the object will be two-dimensionally guided by the boundary or boundries.

The plate can also be equipped with one or two channels, whereby a unidimensional wave is obtained and, at the end of the channel, directed towards a receiver. The channels are feasible by changing the plate structure, e.g. the thickness. They can also be formed by using different types of adjoining materials, namely in a manner similar to optical wave guides, wherein the core of the guide and the envelope surrounding the core can consist of different materials.

The thickness of the plate equals ⅓ to 3 mm and depends on the wave length. Namely it has been found that the most favorable measurements for the plate thickness lie within a range which is 5–10 times bigger than the wave length of the generated ultrasonic waves. If channels are provided in the plate, their diameter has also to be kept 5 to 10 times bigger than the wave length of the used ultrasonic waves. Furthermore the unidimensional guidance has the advantage that the signals arrive one after another and are also detected in this succession. It is also possible to use thicker plates.

Compared to the known devices, the device of the invention offers the advantage of a flat construction with reproducible and accurate analysis data. In addition the construction is considerably simplified, since the liquid-filled housing can be eliminated. The propagation of the ultrasonic waves is guaranteed within the plate-shaped solid body, so that additional steps become superfluous. This fact makes also possible the use of small devices, e.g. of the size of a key. Furthermore it is possible to produce also devices with large dimensions, which can analyze the structure of the object, as well as its position, which can be advantageous for instance for the control of computers, similar as in the known contact fields (touch panels)and the detection of larger objects, e. g. the whole hand.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
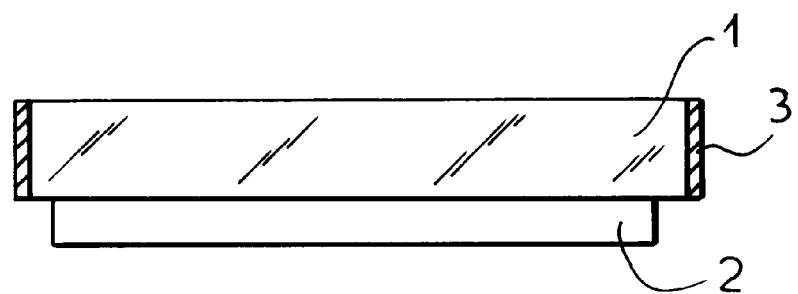
FIG. 1 is a lateral view of the device in a schematic representation.

In the represented example FIG. 1 shows a round plate 1 with transducers 3 arranged on the rim and a transducer 2 arranged underneath the plate. In the embodiment shown in FIG. 2 in a top view, it can be seen that transducers 4 and 5 are arranged all around the plate. The transducers can function as senders, as well as receivers. The optional bottom transducer 2 can not be seen in FIG. 2.

Figure 2:
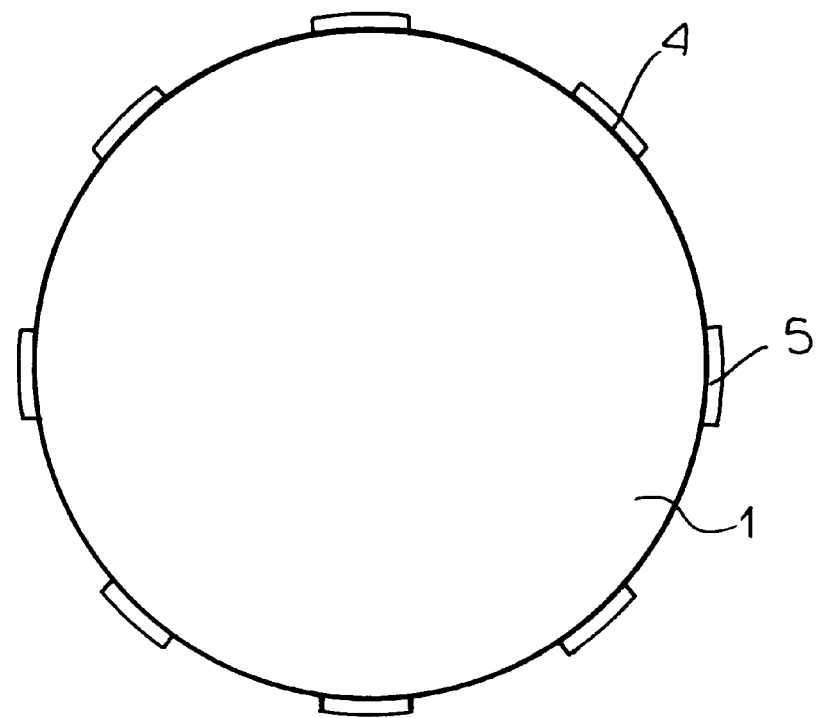
FIG. 2 is a top view of the embodiment shown in FIG. 1.

In this device schematically represented in FIGS. 1 and 2, shear waves in the ultrasonic range are used, which propagate in the plate (the solid body) along one or also both surfaces.

Figure 3:
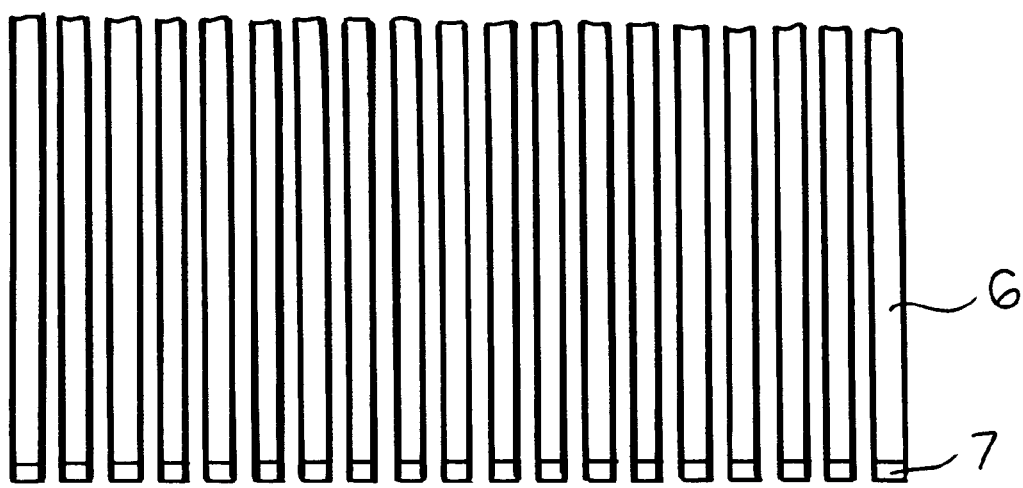
FIG. 3 is an elevational view the arrangement of a plate consisting of unidimensional wave guides.
Figure 4:
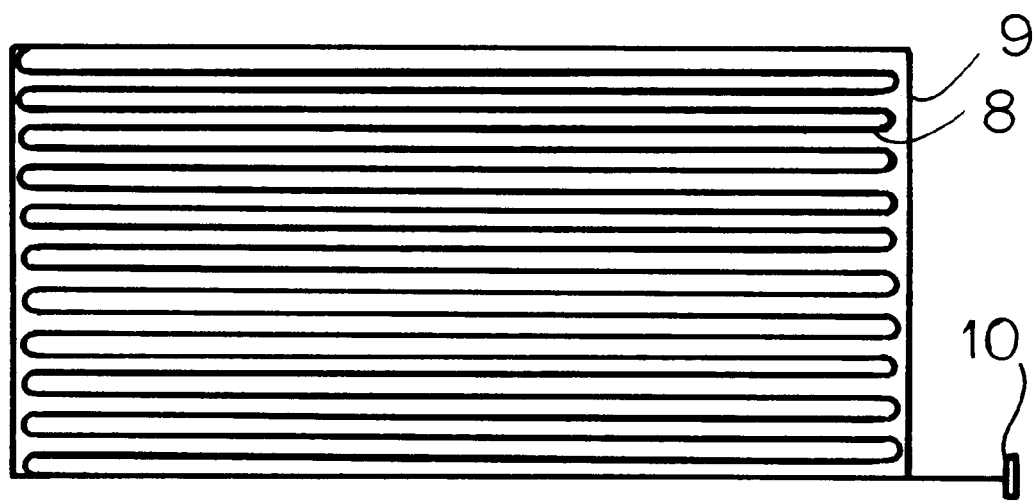
FIG. 4 is a diagram showing the channel path through a plate.
Figure 5:
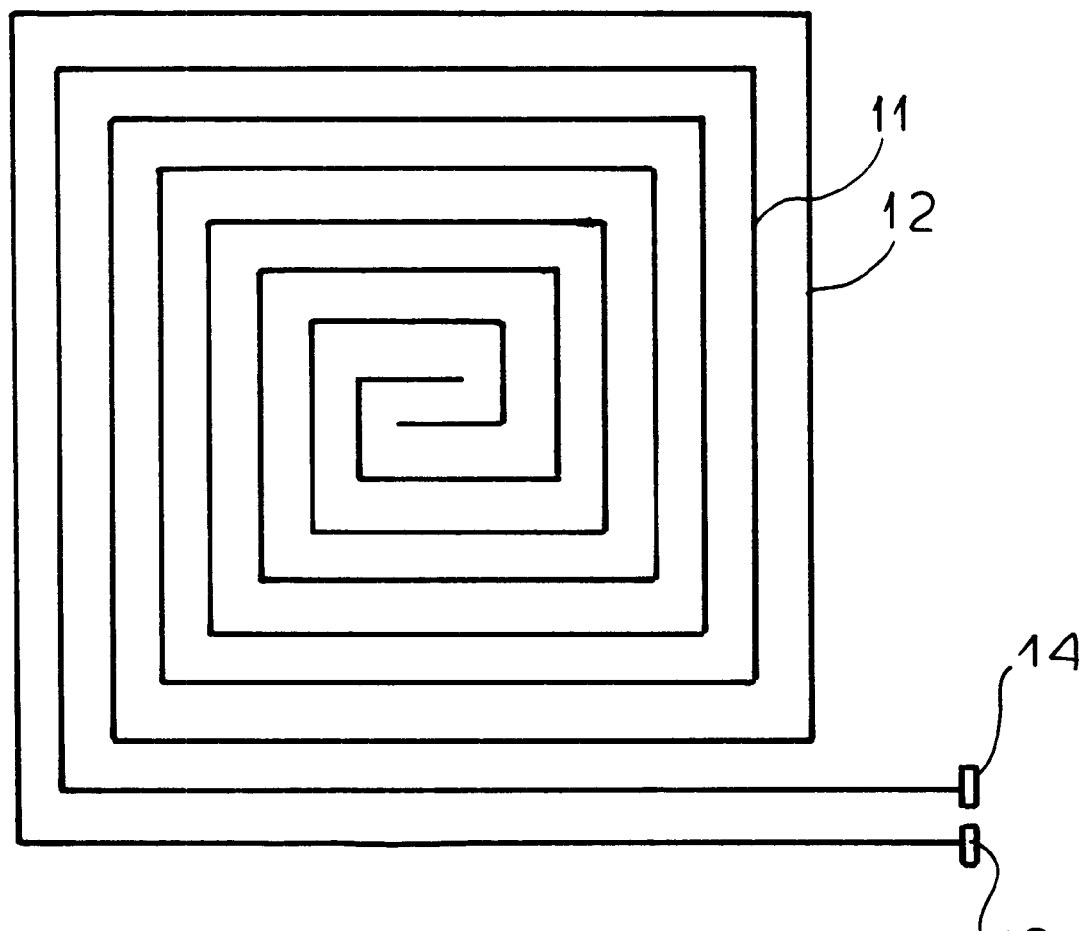
FIG. 5 is a diagram showing the spiral-shaped arrangement of two channels in a plate.

Consequently these are guided waves, i.e. of the type which can not spread in all dimensions. In the plate of the embodiment examples of FIGS. 1 and 2, two-dimensional waves are produced, while plates with channels of any origin, as for instance in FIGS. 3, 4 and 5, show waves with unidimensional spreading.

Similar to the known devices using bulk waves, the electric signals are transmitted from the receiving transducer, via an amplifier, and possibly a detector with the assistance of a analog/digital converter to a computer which, based on that, delivers the information about the structure and/or the position of the analyzed stratum.

The method of analysis used in the case of two-dimensional waves corresponds to the one used in the previously mentioned bulk-waves devices, e.g. the radon transformation. Furthermore the version with channels offers a simpler possibility, because it is only necessary to summarize the signal, respectively signals which correspond to the channel path.

Naturally these methods are only then necessary, when it is desired to reproduce the image of the examined layer. For other purposes it is also possible to use other signal processing methods, e.g. a simple signal comparison, other types of transformation, etc.

Moreover the flat solution of the device according to the invention offers a simple possibility of structure detection and of the therewith connected position detection, since the plate also allows for a unidimensional wave guidance. The advantage of an analysis with unidimensional wave guidance consists in that it makes line scanning possible.

For producing unidimensional waves, as shown in FIG. 3 the plate has channels 6 running parallel next to each other, whose lateral walls are connected with neighboring channels. At their ends the channels 6 have transducers, which send in sequence and transform the received ultrasonic waves into signals.

In FIG. 4 a channel 8 is shown which covers the entire surface of a plate 9 and which transmit to the transducer 10 the information of the object exposed to the ultrasonic waves.

FIG. 5 shows two parallel channels 11 and 12, which follow an angular-spiral path and receive the backscattered ultrasonic waves directing them to the transducers 13 and 14, which further transmit to the computer the signals resulting therefrom.

The represented shapes of the channel path are indicated only as examples, because each path shape is suited to transmit unimodally the backscattered waves to a transducer.

What is claimed is:

1. A method of analyzing a structure, comprising the steps of:

(a) providing a plate-shaped solid body of an ultrasonic-wave-propagating material;

(b) placing an object on a surface of said body having a structure in contact with said surface to be analyzed;

(c) launching into said body from a side thereof horizontally polarized ultrasonic shear waves generally along said surface whereby said horizontally polarized ultrasonic shear waves propagate in said body and interact with said structure to produce reflected and back-scattered waves which propagate in said body;

(d) acquiring said reflected and back-scattered waves at a side of said body; and (e) determining characteristics of said structure from the acquired reflected and back-scattered waves.

2. A device for analyzing a structure which comprises:

a plate-shaped solid body of an ultrasonic-wave-propagating material, and having a thickness inducing ultrasonic wave propagation in said body along a surface thereof upon which an object having aa thickness inducing ultrasonic wave propagation in said body along a surface thereof upon which an object having a structure to be analyzed is placed;

at least one transducer located along at least one side of said body for launching into said body from a side thereof horizontally polarized ultrasonic shear waves propagating generally along said surface and interacting with said structure to produce reflected and back-scattered waves which propagate in said body; and at least one transducer along a side of said body for acquiring reflected and back-scattered waves propagating in said body for determining characteristics of said structure from the acquired reflected and back-scattered waves.

3. The device defined in claim 2 wherein said body consists of a metal or crystal with low ultrasonic absorption.

4. The device defined in claim 2 wherein said body is formed with at least one channel constituting a waveguide for said horizontally polarized ultrasonic shear waves.

5. The device defined in claim 4 wherein a plurality of channels are formed in said body.

6. The device defined in claim 5 wherein said channels are formed of different materials.

7. The device defined in claim 5 wherein said channel has a core made of one material and an envelope of another material.

8. The device defined in claim 2 wherein one of said transducers is located along a lateral edge of said body and another of said transducers is located on an opposite side of said body from said surface.

9. The device defined in claim 2 wherein said body has a thickness of ⅓ to 3 mm.

10. The device defined in claim 2 wherein said body is formed with a plurality of channels having transducers at ends thereof which are scanned successively.

11. The device defined in claim 2 wherein said body is formed with a channel for said horizontally polarized ultrasonic shear surface which has a spiral configuration.

12. The device defined in claim 2 wherein said body is formed with at least one channel for said horizontally polarized ultrasonic shear wave having channel parts running back and forth in said body.

* * * * *